United States Patent
Groeschke et al.

(10) Patent No.: US 10,286,156 B2
(45) Date of Patent: *May 14, 2019

(54) MONITORING DEVICE FOR MONITORING OPERATION OF A DRUG DELIVERY DEVICE

(71) Applicant: Sanofi-Aventis Deutschland GmbH, Frankfurt am Main (DE)

(72) Inventors: Jasmin Groeschke, Frankfurt am Main (DE); Alexander Allerdings, Frankfurt am Main (DE); Jan-Peter Spengler, Frankfurt am Main (DE); Christoph Dette, Frankfurt am Main (DE); Matthias Scharf, Frankfurt am Main (DE); Andreas Bode, Frankfurt am Main (DE); Michael Schrack, Pliezhausen (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/701,064

(22) Filed: Sep. 11, 2017

(65) Prior Publication Data

US 2017/0368265 A1 Dec. 28, 2017

Related U.S. Application Data

(63) Continuation of application No. 14/378,060, filed as application No. PCT/EP2013/052510 on Feb. 8, 2013, now Pat. No. 9,782,543.

(30) Foreign Application Priority Data

Feb. 13, 2012 (EP) .................................... 12155205

(51) Int. Cl.
*A61M 5/315* (2006.01)
*A61M 5/24* (2006.01)
(Continued)

(52) U.S. Cl.
CPC .......... *A61M 5/31568* (2013.01); *A61M 5/24* (2013.01); *A61M 5/3155* (2013.01);
(Continued)

(58) Field of Classification Search
CPC .. A61M 2005/3125; A61M 2005/3126; A61M 2005/3142; A61M 2205/14;
(Continued)

(56) References Cited

U.S. PATENT DOCUMENTS 5,651,775 A * 7/1997 Walker .................... G06F 19/00
604/207
9,782,543 B2 * 10/2017 Groeschke ............. G01B 21/16
(Continued)

FOREIGN PATENT DOCUMENTS

WO 2004/078239 9/2004
WO 2004/078240 9/2004
(Continued)

OTHER PUBLICATIONS

International Search Report for International Application No. PCT/EP2013/052510, completed Apr. 8, 2013.
(Continued)

*Primary Examiner* — Brandy S Lee
(74) *Attorney, Agent, or Firm* — Fish & Richardson P.C.

(57) ABSTRACT

The present invention relates to a monitoring device for monitoring operation of a drug delivery device and to a respective drug delivery device, wherein the monitoring device comprises:
a fastening member (32) to releasably attach the monitoring device to an axially elongated housing (14) of the drug delivery device (10),
(Continued)

a sliding member (40) shiftable relative to the fastening member (32) in an axial direction (1, 2) and being adapted to operably engage with at least one dose setting component (17, 18, 26) of the drug delivery device (10) to follow an axial displacement of the dose setting component (17, 18, 26) relative to the housing component (14), a first sensor arrangement (36, 46) for detecting a rotation of the dose setting component (17, 18, 26) relative to the fastening member (32), a second sensor arrangement (38, 48) for detecting an axial displacement of the sliding member (40) relative to the fastening member (32), and a processing member (34) coupled to the first and to the second sensor arrangements (36, 38) to process first and second signals obtainable from the first and from the second sensor arrangements (36, 38, 46, 48) for determining the size of a dose dispensed by the drug delivery device (10).

15 Claims, 4 Drawing Sheets

(51) Int. Cl.
*G01B 21/16* (2006.01)
*A61M 5/31* (2006.01)
*G06F 19/00* (2018.01)

(52) U.S. Cl.
CPC .... *A61M 5/31525* (2013.01); *A61M 5/31551* (2013.01); *G01B 21/16* (2013.01); *A61M 5/3129* (2013.01); *A61M 2005/3125* (2013.01); *A61M 2005/3126* (2013.01); *A61M 2005/3142* (2013.01); *A61M 2205/14* (2013.01); *A61M 2205/215* (2013.01); *A61M 2205/3306* (2013.01); *A61M 2205/3317* (2013.01); *A61M 2205/3569* (2013.01); *A61M 2205/3592* (2013.01); *A61M 2205/50* (2013.01); *A61M 2205/502* (2013.01); *A61M 2205/52* (2013.01); *A61M 2209/04* (2013.01); *G06F 19/3468* (2013.01)

(58) Field of Classification Search
CPC .... A61M 2205/215; A61M 2205/3306; A61M 2205/3317; A61M 2205/3569; A61M 2205/3592; A61M 2205/50; A61M 2205/502; A61M 2205/52; A61M 2209/04; A61M 5/24; A61M 5/3129; A61M 5/31525; A61M 5/3155; A61M 5/31551; A61M 5/31568; G01B 21/16; G06F 19/3468

See application file for complete search history.

(56) References Cited

U.S. PATENT DOCUMENTS

| | | |
|---|---|---|
| 2004/0207385 A1 | 10/2004 | Gafner et al. |
| 2009/0318865 A1 | 12/2009 | Moller et al. |
| 2011/0313349 A1 | 12/2011 | Krulevitch et al. |

FOREIGN PATENT DOCUMENTS

| | | |
|---|---|---|
| WO | 2004/078241 | 9/2004 |
| WO | 2010/037828 | 4/2010 |
| WO | 2010/052275 | 5/2010 |
| WO | 2010/098927 | 9/2010 |
| WO | 2010/128493 | 11/2010 |
| WO | 2011/117212 | 9/2011 |

OTHER PUBLICATIONS

International Preliminary Report on Patentability in International Application No. PCT/EP2013/052510, dated Aug. 9, 2014, 9 pages.

* cited by examiner

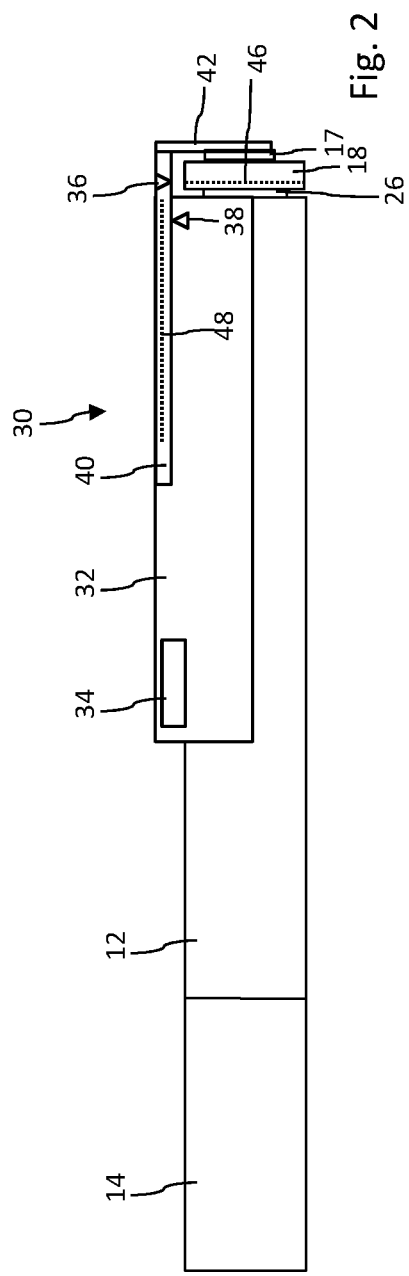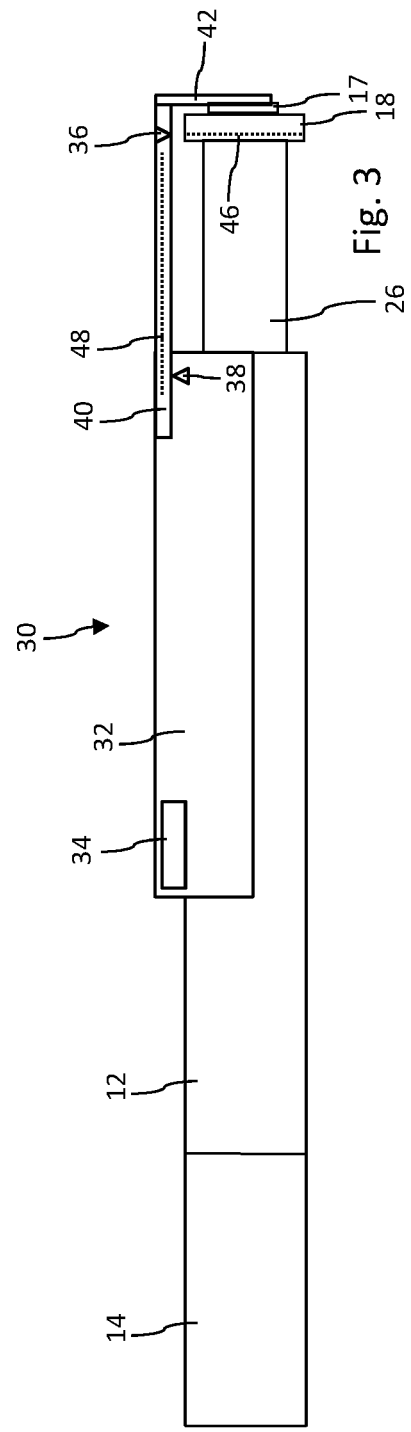

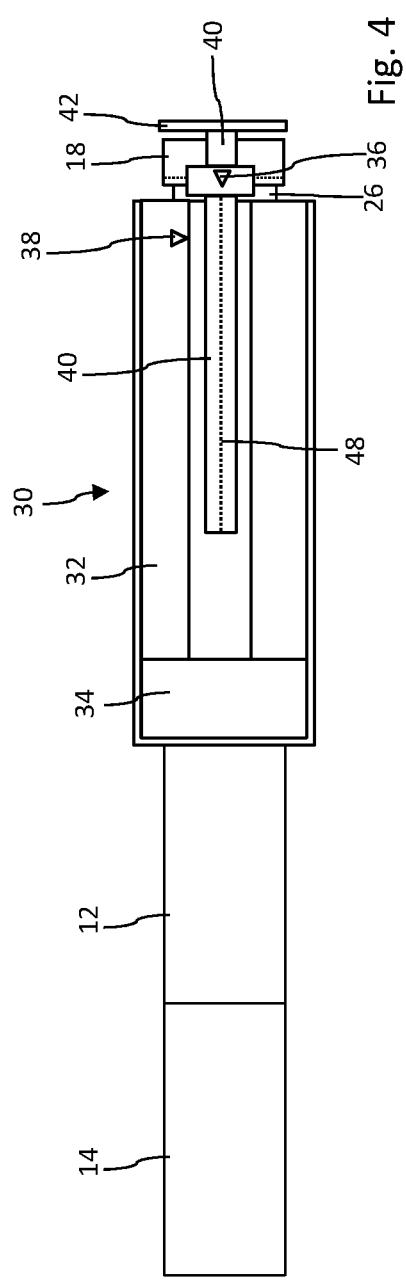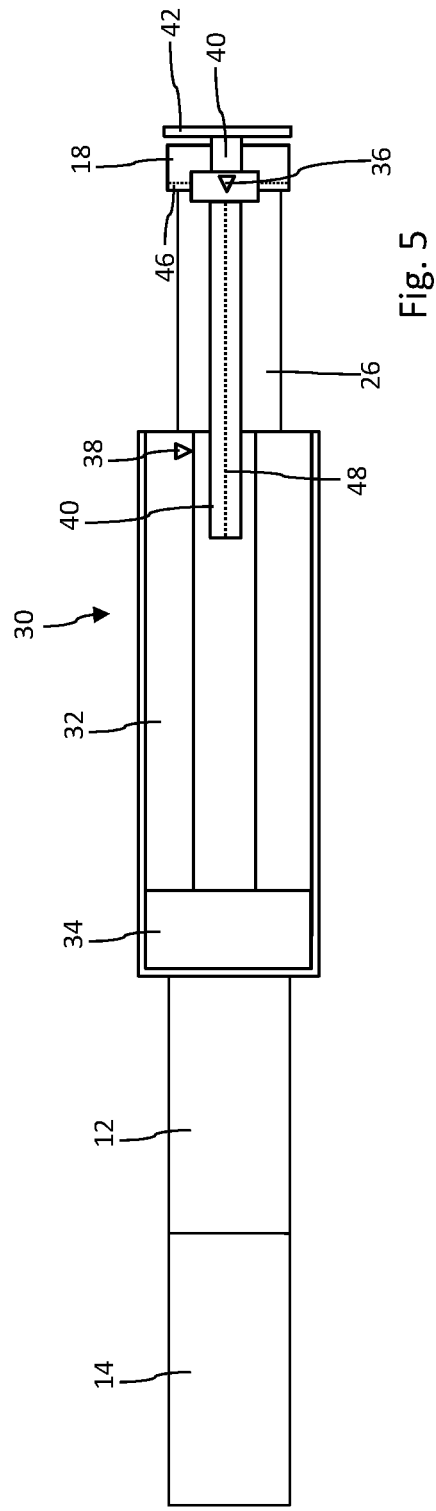

US 10,286,156 B2

MONITORING DEVICE FOR MONITORING OPERATION OF A DRUG DELIVERY DEVICE

CROSS REFERENCE TO RELATED APPLICATIONS

The present application is a continuation of U.S. patent application Ser. No. 14/378,060 filed Aug. 11, 2014, which is a U.S. National Phase Application pursuant to 35 U.S.C. § 371 of International Application No. PCT/EP2013/052510 filed Feb. 8, 2013 which claims priority to European Patent Application No. 12155205.3 filed Feb. 13, 2012, the entire contents of which are incorporated entirely herein by reference.

FIELD OF THE INVENTION

The present invention relates to the field of drug delivery devices and in particular to injection devices designed and intended for regular and long-term self-medication. In particular, the invention refers to a monitoring device adapted to monitor and to log or to record long-term usage and handling of the drug delivery device.

BACKGROUND AND PRIOR ART

Chronic diseases generally require administering of medicaments or drugs according to a pre-defined time schedule in order to keep the concentration level of a pharmaceutically active substance on a pre-defined level. Many medicaments require administration by way of injection by making use of syringes or syringe-like drug delivery devices. Such devices should be universally applicable and should be operable even by persons without formal medical training.

Moreover, such devices, like pen-type injectors should provide accurate, precise and reliable setting of a dose and subsequent dispensing of the respective medicament. Typically, the medicament to be dispensed and injected is provided in a disposable or replaceable cartridge, such as a vial, an ampoule or a carpule comprising a slidably disposed piston to become operably engaged with a piston rod of a drive mechanism of the drug delivery device. The drive mechanism is adapted to apply thrust to the cartridge's piston in distal direction in order to build-up a respective fluid pressure, which in turn leads to a dispensing of the liquid medicament via a dispensing or distal end of the cartridge being typically in fluid connection with a piercing element like an injection needle.

It is generally of importance, that the patient strictly follows a given prescription schedule. However, patients that already got used to the medicament for a long time or patients that suffer side effects of a chronic disease and which may be physically or even cognitively impaired, compliance of the prescription schedule is sometimes sub-optimal. Since a large variety of existing drug delivery devices is implemented all-mechanically, it is further rather difficult for an attending physician to control, whether the patient strictly follows a given prescription schedule.

Document WO 2010/098927 A1 describes a medical module for a drug delivery pen configured to be attached to a disposable drug delivery pen so that the module may determine: selected dosage, injection of selected dosage, duration of injection, time of injection and other injection-related parameters. The medical module comprises a dosage sensor coupled to a primary module housing and a follower portion connected to the dosage sensor and disposed for movement relative to the primary module housing. Furthermore, retention forks are provided that are connected to the follower portion. Said retention forks are configured to capture an actuation button of a drug delivery pen there between.

The dosage sensor is preferably a linear potentiometer and is used to measure the position of a dosage selector of the drug delivery pen for determining the size of a bolus injected by a user. When the drug delivery device comprises a rotatable and axially displaceable dose setting component, like a dosage selector being operable in a screw-like manner, it is suggested to frictionally couple the dosage selector of the pen with a capture ring which in turn is coupled to a follower. The capture ring may further be provided with external splines or teeth that are in engagement with internal splines or teeth of a rotatable knob. This knob is provided with a through opening to allow actuation button of the pen to protrude through the opening for engagement by the user.

Hence, the medical module comprises numerous mechanically interacting components to mechanically couple the medical module with a dosage selector of the pen injector. The module therefore comprises a comparatively large number of mutually interacting mechanical components, which may become prone to failure.

OBJECTS OF THE INVENTION

It is therefore an object of the present invention to provide a mechanically simplified monitoring device adapted to monitor and to log operation of a manually operated drug delivery device allowing for a rather simple but reliable, durable and robust handling. Additionally, the monitoring device should be able to properly distinguish between different operation modes of the drug delivery device. Moreover, the monitoring device should provide almost full and direct access to user-operable components of the drug delivery device, even when attached thereto, for not hindering a user in his convenient handling of the drug delivery device.

SUMMARY OF THE INVENTION

In a first aspect, a monitoring device for monitoring operation of a drug delivery device and in particular of a pen-type injector is provided. The monitoring device comprises a fastening member to releasably attach the monitoring device to a housing of the drug delivery device. Moreover, the monitoring device comprises a sliding member being shiftable or displaceable relative to the fastening member at least along a longitudinal or axial direction. The sliding member is further adapted to operably engage with at least one dosing arrangement of the drug delivery device in order to follow an axial displacement of the dosing arrangement relative to the housing component of the drug delivery device.

The monitoring device further comprises a first sensor arrangement for directly detecting a rotation or rotative movement of the dosing arrangement of the drug delivery device relative to the fastening member and further comprises a second sensor arrangement for directly detecting an axial displacement of the sliding member relative to the fastening member. Hence, the first sensor arrangement is exclusively sensitive to a relative rotational displacement of the dosing or dose setting arrangement relative to the housing of the drug delivery device and/or relative to the fastening member of the monitoring device. The second sensor is exclusively sensitive to an axial displacement of the dosing or dose setting arrangement relative to the housing of the drug delivery device and/or relative to the fastening member of the monitoring device.

The monitoring device also comprises a processing member coupled to the first and to the second sensor arrangements to process first and second signals obtainable from the first and from the second sensor arrangements in order to determine the size of a dose actually dispensed by the drug delivery device. By providing a first and a second sensor arrangement, both a rotational but also a longitudinal or axial displacement of the at least one dosing arrangement of the drug delivery device relative to the housing can be precisely determined. This way, a dose setting but in particular a dose dispensing procedure executable by the drug delivery device can be detected and recorded in a redundant way. Moreover, by means of a first and second sensor arrangements adapted to detect different types of relative movement between the at least dosing arrangement relative to the housing of the drug delivery device or relative to the fastening member, the monitoring device can precisely distinguish between a dose dispensing and a dose setting procedure.

By means of the first and the second sensor arrangement an axial displacement and rotational displacement of one and the same dose setting component of the drug delivery device can be independently measured and quantitatively determined. Besides to provide a certain redundancy the signals provided by the two sensors can be compared to distinguish between different configurations of the drug delivery device, in particular to distinguish between a dose setting and a dose dispensing procedure.

Furthermore, by making use of first and second sensor arrangements, the internal mechanical construction of the monitoring device can be simplified, rendering the monitoring device particularly robust, reliable, durable and failure-safe.

The monitoring device is particularly adapted to be releasably coupled to a particular type of drug delivery device, preferably to a disposable pen-type injector. Hence, when the disposable drug delivery device has to be disposed, the monitoring device can be disassembled therefrom and can be releasably attached to another drug delivery device, thereby providing a continuous detecting, recording and storing of medication-related data, such like selected dose size, injected dose size, duration of injection, time of injection and so on.

The sliding member of the monitoring device is particularly adapted to become operably engaged with the at least one dosing arrangement of the drug delivery device, which is operable to be displaced in proximal direction for dose setting purposes and which is to be displaced in opposite, hence distal direction, for dispensing of a dose.

The dosing arrangement typically comprises a dose dial sleeve threadedly engaged with a drive mechanism of the drug delivery device. Near a proximal end of the dose dial sleeve there is typically provided a dose dial member by way of which the dose dial sleeve can be gripped and rotated by a user for setting of a dose. Additionally, the dosing arrangement comprises a dose butting providing a proximal end face of the dosing arrangement by way of which a user-induced dose dispensing procedure can be triggered and controlled.

In a preferred embodiment, the first sensor arrangement and/or the second sensor arrangement is adapted to quantitatively determine a rotational and/or axial displacement of the dosing arrangement of the drug delivery device relative to the housing of the drug delivery device and/or relative to the fastening member of the monitoring device when releasably attached to said housing. At least one of the two sensor arrangements is therefore adapted to determine the size or the path length of a relative axial and/or rotational displacement between the dosing arrangement and the housing of the drug delivery device. Here, the axial displacement and the rotational displacement alone may each be directly indicative of the size of a set dose or of a dispensed dose. Moreover, the size of a dose may also be determined on the basis of a combination of measured axial and rotational displacements.

In particular, the first sensor arrangement is adapted to quantitatively determine a rotational displacement of the dose setting component relative to the housing of the drug delivery device and/or relative to the fastening member. The second sensor arrangement in turn is adapted to quantitatively determine an axial displacement of the dose setting component relative to the housing of the drug delivery device and/or relative to the fastening member.

It is of further benefit and according to another embodiment, when at least one of first and second sensor arrangements comprises a sensor cooperating with a scale or scale member comprising such a scale. Here, the respective sensor and its corresponding scale are intended to become subject to a relative displacement when the dosing arrangement of the drug delivery device is subject to a movement relative to the housing of the drug delivery device. The sensor may be based on a tactile, optical, magnetical or electrical sensor principle. Hence, the scale may be correspondingly encoded so that detectable signals can be generated by the at least one sensor in response of a relative movement between the scale and its corresponding sensor. Typically, the scale and its corresponding sensor both belong to the respective sensor arrangement or build up the same.

The at least one sensor arrangement may be either adapted to determine absolute or relative positions or orientations between the sensor and its corresponding scale or it may be designed to only determine incremental changes of the relative position or orientation between the sensor and its corresponding scale.

In a further preferred embodiment, the first sensor arrangement comprises a first sensor arranged on the sliding member of the monitoring device, which cooperates with a correspondingly designed first scale of the sensor arrangement, which is attachable to a rotatable dose dial member of the drug delivery device. Here, the dose dial member may be provided near a proximal end of the drug delivery device. The dose dial member is typically operable to be rotated in a screw-like manner relative to the housing of the drug delivery device, thereby not only rotating the dose dial member but also axially displacing the dose dial member or the entire dosing arrangement in proximal direction relative to the housing of the drug delivery device.

By providing the first scale on the rotatable dose dial member and by arranging the first sensor on the sliding member of the monitoring device, first sensor and first scale may be fixed relative to each other with regard to the axial direction, thereby enabling the first sensor to exclusively detect and to sense a rotational movement of the dose dial member that serves as a dose setting component of the drug delivery device. The angular distance of the dose dial member between an initial configuration and a proximally extended configuration is directly indicative of the size or magnitude of the selected dose.

Typically, during a subsequent and distally directed dose dispensing procedure, the dose dial member rotates in the opposite direction, thereby decrementing the angular distance between initial and extended configuration.

In another preferred embodiment, the monitoring device further comprises a second sensor arrangement having a second sensor arranged on the fastening member and cooperating with a second scale of the sensor arrangement attachable on the sliding member or being actually attached thereto. Here, also an alternative embodiment is conceivable, wherein the second sensor is arranged on the sliding member and wherein the second scale is arranged on the fastening member. However, only the relative displacement between the second sensor and its cooperating or corresponding fastening member is of relevance.

Since the sliding member is designed for a purely longitudinal translational displacement with respect to the fastening member, the second sensor arrangement is accordingly adapted to sense and to detect a corresponding longitudinal or axial displacement between the second sensor and its corresponding second scale.

In effect, by means of the first and second sensor arrangements, a screw like motion of the dosing arrangement, in particular of its dose setting and/or dose dispensing component can be separately detected and measured in terms of a longitudinal or axial displacement and in terms of a rotational displacement. Apart from providing a redundancy this separate detection of an angular and a translational movement of the dosing arrangement, in particular of its dose setting and/or dose dispensing component can be further exploited to increase accuracy of the dose size determination as well as to precisely distinguish between a dose setting and a subsequent dose dispensing procedure, which are both to be conducted by the dose setting or dispensing component.

According to another preferred embodiment, the sliding member comprises an engaging member at a proximal end to axially abut with a dose button of the drug delivery device located at the proximal end of the drug delivery device. While the sliding member substantially extends in axial direction and is radially spaced from the drug delivery device, the engaging member comprises a planar or flange-like shape and extends radially inwardly from a proximal end of the sliding member in order to axially abut with the dose button of the drug delivery device. Here, an abutment face of the engaging member facing in distal direction is adapted to abut against a proximal face of the dose button facing in proximal direction.

The engaging member may either cover the entire proximal face of the dose button and may effectively serve as an intermediate component when the dose button is to be depressed in distal direction by a user during a dose dispensing procedure. However, the engaging member may also comprise a ring-like shape featuring a through opening, which allows to directly access the dose button located underneath.

Since the rotational movement of a dose dial of the drug delivery device is to be detected by means of the first sensor arrangement, a frictional engagement of the monitoring device with a dose dial member of the drug delivery device is generally not required. It is only intended that the engaging member of the sliding member of the monitoring device gets in axial abutment configuration with the dose button of the drug delivery device upon mutual assembly of the monitoring device and the drug delivery device. Consequently, the dose dial member of the drug delivery device is directly accessible to the user, thus enhancing the patient's acceptance to make use of the monitoring device.

In a further preferred embodiment, the first and/or the second scale of first and second sensor arrangements, respectively, is incrementally encoded in a direction of movement relative to the first and/or second sensor. This way, the sensor of first and/or second sensor arrangements is applicable to determine an incremental displacement between first and/or second sensors relative to their corresponding first and/or second scales, respectively. This way, the monitoring device does not generally require a particular reset or calibration when assembled to a drug delivery device.

Once the monitoring device has been correctly assembled and fastened to the housing of the drug delivery device, any detectable movement of the dose setting or dose dispensing component of the drug delivery device can be incrementally detected, monitored and stored.

According to another embodiment, the processing member of the monitoring device is adapted to distinguish between a dose setting and a dose dispensing procedure of the drug delivery device on the basis of a comparison of first and second signals obtainable from the first and the second sensor arrangements, respectively. Here, the comparison of first and second signals is closely correlated to specific properties of the drive mechanism of the respective drug delivery device. For instance, with the device as illustrated in WO 2004/078239 A1, WO 2004/078240 A2 or WO 2004/078241 A1, the dose setting or dose dispensing component of the drug delivery device may be subject of a small but detectable axial and distally directed non-rotational displacement at the very beginning of a user-initiated dose dispensing procedure.

Such a purely translational but non-rotational displacement is due to a clutch mechanism of the drive mechanism of the drug delivery device. By means of such a clutch mechanism, axial and distally directed displacement of a dose button can be transferred into a corresponding distally directed displacement of the piston rod of the drive mechanism, thereby exerting a dose-dispensing thrust on the piston of a cartridge arranged in the drug delivery device. However, if for some reason the dispensing procedure is interrupted, e.g. by releasing the dose button prior to arrive at an initial configuration, the clutch mechanism may become repeatedly active and may serve to at least slightly displace the released dose button towards the proximal direction in a non-rotational way.

Depending on the particular configuration of the clutch mechanism of the drug delivery device, the device is either in a dose dispensing or in a dose setting mode. Transfer between the two modes is always accompanied by a distally or proximally but non-rotational displacement of the dosing arrangement, of its dose dial member and its dose button, which is accordingly detected by the two-sensing arrangements. By continuously comparing the first and second signals obtainable from first and second sensor arrangements, activation and deactivation of the clutch mechanism together with a respective transfer regarding dose setting or dose dispensing mode can be precisely detected.

In a further preferred aspect, such a change of the operation mode of the drive mechanism of the drug delivery device comes along with an asynchronism between the first signal and the second signal of first and second sensor arrangements, respectively. Then, the signals independently obtainable from the first and the second sensor arrangement exhibit at least one characteristic deviation. The signal of the first sensor is at least temporally uncorrelated to the signals of the second sensor and/or vice versa. In such situations the signals may be classified to be asynchronous. Such asynchronism is therefore indicative of a beginning and/or of an end of a dose dispensing procedure of the drug delivery device. Furthermore, it is intended, that the monitoring device is particularly adapted to monitor and to record at least the dose dispensing procedures, hence the time of dose dispensing procedure as well as the size of the dose dispensed. By precisely distinguishing between a dose setting and a dose dispensing procedure, also a correction of a dose setting prior to execute a dose dispensing procedure can be detected and taken into account.

Moreover, not only said asynchronism but also a temporal offset between first and second signals may be indicative of a beginning and/or of and end of a dose dispensing procedure. Therefore, in a further or alternative embodiment, the temporal offset between first and second signals can be used as a trigger to start and/or to stop monitoring, logging or recording of a dose dispensing procedure by the monitoring device and its processing member.

In a further preferred embodiment, the processing member of the monitoring device is adapted to record and/or to store the size and/or the time or any other health- or medication related parameters of a dose dispensing procedure. Preferably, recording and/or storing of size, time or said other dose-dispensing related parameters is recorded and/or stored only by the processing member when receiving the first signal from the first sensor arrangement in synchrony with the second signal obtained from the second sensor arrangement. A particular singularity of one sensor signal compared to the second sensor signal may be thus indicative of the beginning or end of a dose dispensing and/or dose setting procedure. The continuous surveillance and processing of signals of first and second sensor arrangements is therefore applicable to distinguish between a dose setting and dose dispensing configuration of the drug delivery device.

If only signals from one of the two sensor arrangements are received by the processing member, the respective signals are not further processed for determination of e.g. the size of a dose. Additionally, if a temporal offset between first and second signal is above a predefined threshold, this may serve as an indication that some kind of error or malfunction has occurred, which requires maintenance or replacement of the monitoring device. Consequently, the monitoring device may further comprise an alert means, by way of which a user can be audibly, visually or heptically alerted.

Generally, the processing member, which may comprise a microcontroller or some other kind of electronic signal processing device comprises a storage to store recorded data and further has a communication member to transfer the recorded data to some kind of analyses tool, by way of which long-term use of the drug delivery device can be illustrated to a patient or physician or other medical staff. The communication member may comprise wireless communication means and may be based on various applicable communication protocols, such like Bluetooth or IEEE 802.11.

Moreover, the monitoring device comprises a power supply, typically in form of a battery, which may be optionally rechargeable even by means of an external or internal solar cell device. In effect, the communication member may be adapted to communicate with a large variety of different analysis tools and devices. It may comprise a communication interface to transfer the stored data either to a computer, to a smartphone or to other analysing devices, e.g. to a tablet computer, that may further process and evaluate the data retrieved from the monitoring device.

The monitoring device may also comprise a digital display in order to indicate to a user the detected or measured dispensing parameters, like time and size of a dispensed dose of the medicament. The display may comprise an electronic display controlled by the processing member.

Additionally, the monitoring device may also comprise one or several input-output means, e.g. in form of keys for setting and configuring the monitoring device according to preferences of a particular user.

In a further preferred aspect, the monitoring device may also comprise an alert function indicating to a user that either a next dispensing or injection of the medicament is due or is already overdue. Additionally, the alert function may indicate to the user, when the injected or set amount of the medicament does not match with e.g. a predefined medication schedule or that a recent injection was not carried out correctly.

The display of the monitoring device may even entirely replace a mechanical display means of the drug delivery device and may therefore mimic its visual appearance.

In a further preferred aspect, the monitoring device may be also equipped with an inertial sensor, by way of which a smooth shaking or twisting of the drug delivery device prior to a dose setting- and dispensing action can be detected. Such a twisting or shaking motion may be necessary in order to prepare and/or to sufficiently mix the liquid medicament provided in the cartridge of the drug delivery device. Additionally, by way of an inertial sensor, a necessary priming of a needle assembly can be detected, which should occur prior to the dose setting and dose dispensing procedure. During priming, the device should point upwards with its distal dispensing end.

Generally, the processing member is electrically connected to any electrical component of the monitoring device, in particular to the first and second sensor arrangements, and to optional components, such like display member, communication member, alert member and/or inertial sensor.

In a further but independent aspect, the invention also relates to a drug delivery device for setting and dispensing of a dose of a medicament. The drug delivery device comprises a housing of substantially tubular shape, which is adapted to accommodate a drive mechanism having a piston rod to operably engage with a piston of a cartridge, which contains a medicament to be dispensed by the drug delivery device. The drug delivery device further comprises at least one dosing arrangement being axially displaceable in a proximal direction for setting of a dose and being subsequently displaceable in an opposite, distal direction to conduct a dose dispensing procedure of the drug delivery device.

Said drug delivery device further comprises a monitoring device as described above, which is releasably attached to the housing of the drug delivery device by its fastening member. The monitoring device is coupled with the drug delivery device in such a way that its sliding member is operably engaged with the dosing arrangement of the drug delivery device. The drug delivery device is preferably of disposable type and may comprise an internal structure as explicitly shown in WO 2004/078239 A1, WO 2004/078240 A2 or WO 2004/078241 A1, which are incorporated herein by reference.

In a preferred embodiment, the dosing arrangement of the drug delivery device comprises a rotatable dose dial member and a dose button. By rotating the dose dial member relative to the housing of the drug delivery device, the entire dosing arrangement becomes subject to a proximally directed screw-like dose setting motion. Hence, the entire dosing arrangement then extends from the proximal end of the housing of the drug delivery device. For dispensing of a dose, the dose button located at a proximal end face of the dosing arrangement is depressible in distal direction, thereby engaging a clutch mechanism of the drive mechanism of the drug delivery device by way of which the user-induced distally directed displacement of the dosing arrangement can be coupled and transferred to a respective distally directed displacement of the piston rod of the drive mechanism, by way of which a predefined amount of the medicament can be dispensed via the opposite, distally located dispensing end of the drug delivery device. During such a distally directed dose dispensing movement of the dosing arrangement, the dose dial member becomes subject to an opposite screw-like motion and returns into its initial position.

In a further preferred embodiment, the drug delivery device also comprises a cartridge holder as a further housing component, which is arranged at a distal end of the proximal housing. The cartridge holder has a cartridge arranged therein, which is at least partially filled with a medicament to be injected. Especially with disposable drug delivery devices, a pre-filled cartridge, of vial- or carpule-like type is readily arranged in the drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,

H-(Lys)5-des Pro36, des Pro37 Exendin-4(1-39)-NH2, des Pro36 Exendin-4(1-39), des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]Exendin-4(1-39), des Pro36 [Met(O)14 Trp(O2)25, IsoAsp28]Exendin-4 (1-39), or des Pro36 [Asp28]Exendin-4(1-39), des Pro36 [IsoAsp28]Exendin-4(1-39), des Pro36 [Met(O)14, Asp28]Exendin-4(1-39), des Pro36 [Met(O)14, IsoAsp28]Exendin-4(1-39), des Pro36 [Trp(O2)25, Asp28]Exendin-4(1-39), des Pro36 [Trp(O2)25, IsoAsp28]Exendin-4(1-39), des Pro36 [Met(O)14 Trp(O2)25, Asp28]Exendin-4(1-39), des Pro36 [Met(O)14 Trp(O2)25, IsoAsp28]Exendin-4 (1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010), H-(Lys)6-des Pro36 [Asp28]Exendin-4(1-39)-Lys6-NH2, des Asp28 Pro36, Pro37, Pro38Exendin-4(1-39)-NH2, H-(Lys)6-des Pro36, Pro38 [Asp28]Exendin-4(1-39)-NH2, H-Asn-(Glu)5des Pro36, Pro37, Pro38 [Asp28] Exendin-4(1-39)-NH2, des Pro36, Pro37, Pro38 [Asp28]Exendin-4(1-39)-

(Lys)6-NH2,

H-(Lys)6-des Pro36, Pro37, Pro38 [Asp28]Exendin-4 (1-39)-(Lys)6-NH2,

H-Asn-(Glu)5-des Pro36, Pro37, Pro38 [Asp28] Exendin-4(1-39)-(Lys)6-NH2,

H-(Lys)6-des Pro36 [Trp(O2)25, Asp28]Exendin-4(1-39)-Lys6-NH2,

H-des Asp28 Pro36, Pro37, Pro38 [Trp(O2)25] Exendin-4(1-39)-NH2,

H-(Lys)6-des Pro36, Pro37, Pro38 [Trp(O2)25, Asp28]Exendin-4(1-39)-NH2,

H-Asn-(Glu)5-des Pro36, Pro37, Pro38 [Trp(O2)25, Asp28]Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28]Exendin-4(1-39)-(Lys)6-NH2, H-Asn-(Glu)5-des Pro36, Pro37, Pro38 [Trp(O2)25, Asp28]Exendin-4(1-39)-(Lys)6-NH2, H-(Lys)6-des Pro36 [Met(O)14, Asp28]Exendin-4(1-39)-Lys6-NH2, des Met(O)14 Asp28 Pro36, Pro37, Pro38 Exendin-4 (1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28]Exendin-4(1-39)-NH2, des Pro36, Pro37, Pro38 [Met(O)14, Asp28]Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28]Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2) 25]Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28]Exendin-4(1-39)-NH2, des Pro36, Pro37, Pro38 [Met(O)14, Trp(O2)25, Asp28]Exendin-4(1-39)-(Lys)6-NH2, H-(Lys)6-des Pro36, Pro37, Pro38 [Met(O)14, Trp (O2)25, Asp28]Exendin-4(S1-39)-(Lys)6-NH2, H-Asn-(Glu)5-des Pro36, Pro37, Pro38 [Met(O)14, Trp(O2)25, Asp28]Exendin-4(1-39)-(Lys)6-NH2, or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, preferred embodiments of the invention will be described by making reference to the drawing, in which:

FIG. 2 shows a schematic side view of the drug delivery device with a monitoring device attached thereto in an initial configuration, FIG. 3 shows the device according to FIG. 2 in an extended configuration after or during setting of a dose, FIG. 4 shows a top view of the device according to FIG. 2, FIG. 5 shows a top view of the device according to FIG. 3

DETAILED DESCRIPTION

Figure 1:
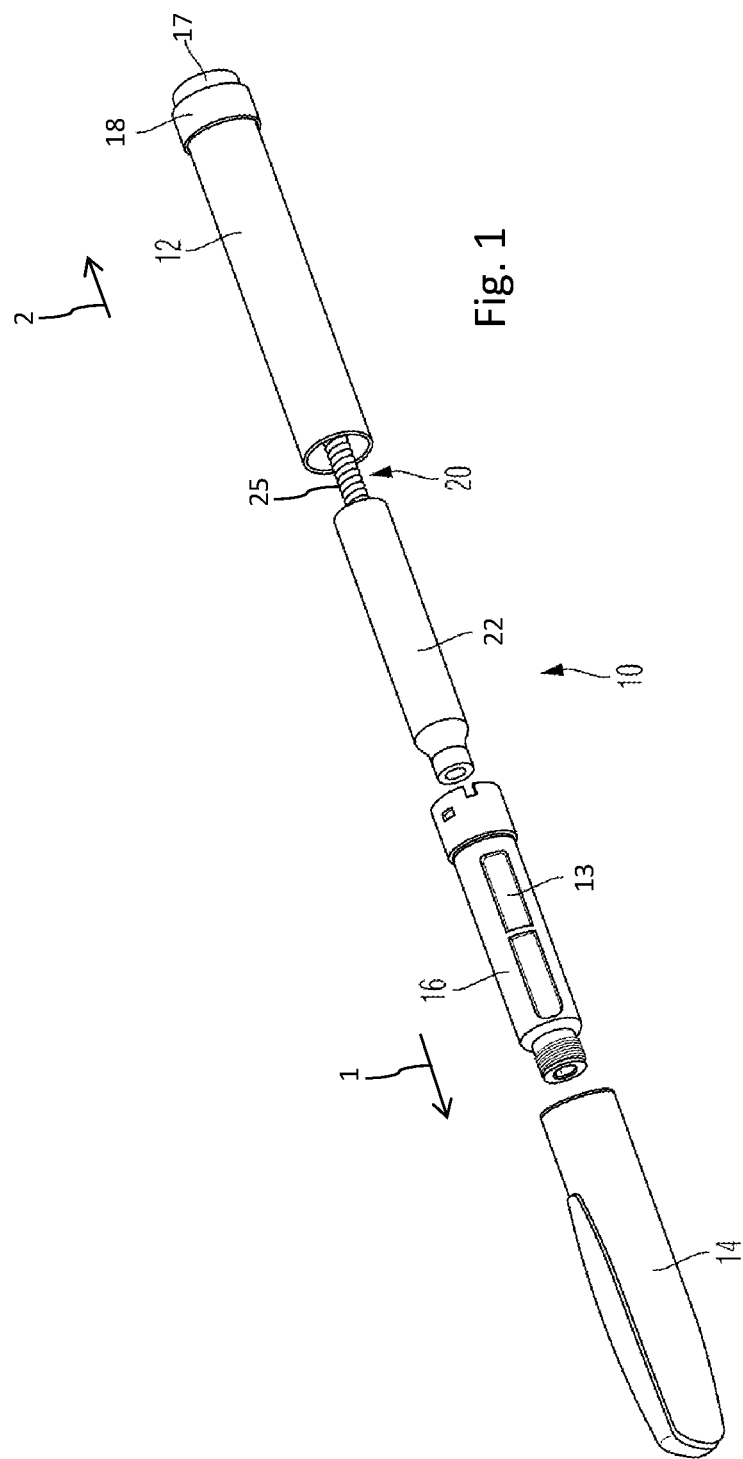
FIG. 1 schematically illustrates a drug delivery device of pen injector type in an exploded view.

In FIG. 1 a drug delivery device 10 in form of a pen-type injector is schematically illustrated, the device 10 is of elongated or substantially tubular shape and comprises three housing components, a proximal main housing 12 or body, a distally located cartridge holder 16 and a releasable protective cap 14 to cover the cartridge holder 16 when the device 10 is not in use. The cartridge holder 16 is adapted to accommodate and to support a cartridge 22 being at least partially filled with the medicament to be dispensed by means of the drug delivery device 10.

The cartridge 22 typically comprises a vial or carpule having a piercable seal or septum at its distal end and further comprises a piston at a proximal end to engage with a piston rod 25 of a drive mechanism 20, which is accommodated and supported in the housing 12. By displacing the piston rod 25 in a distal direction 1 a well-defined amount of the medicament provided in the cartridge 22 can be dispensed via a needle assembly, which is not particularly illustrated here. Typically, a double-tipped needle assembly is to be removably screwed on the threaded socket as shown at the distal end of the cartridge holder 16.

Figure 6:
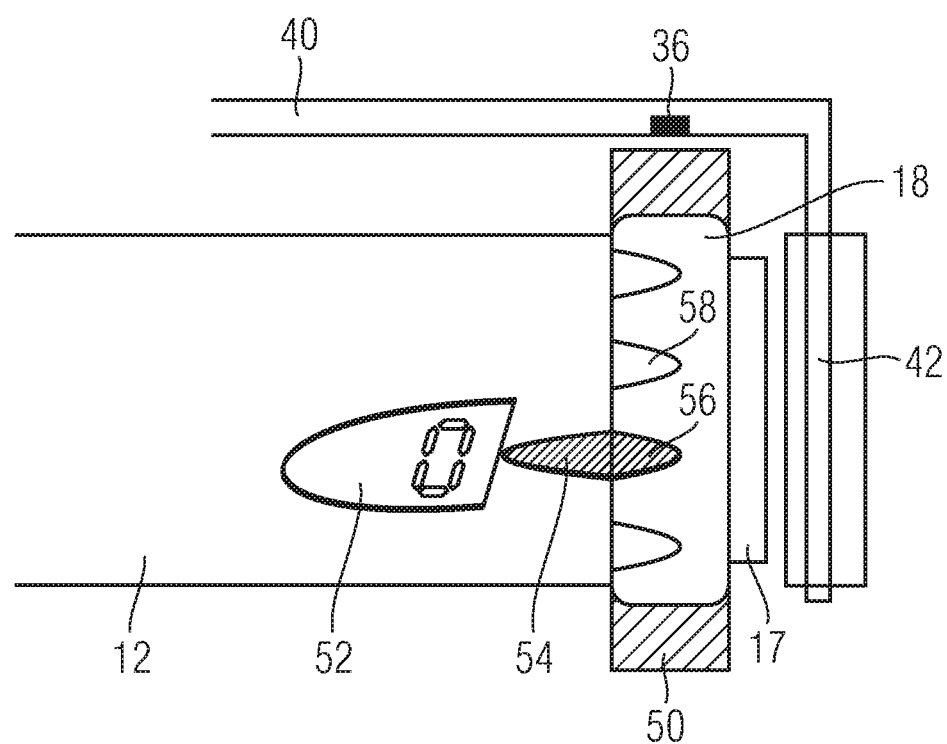
FIG. 6 shows the dosing arrangement of the drug delivery device in an enlarged view in initial configuration.

For inspecting the filling level of the cartridge 22, which is preferably of vitreous type, the cartridge holder 16 comprises at least one lateral inspection window 13. In proximal direction 2, the drug delivery device 10 terminates with a dosing arrangement 26, 18, 17 by way of which a user can individually set and subsequently dispense a dose of the medicament. By means of the dose dial member 18, the entire dosing arrangement as for instance illustrated in FIG. 3 can be screwed out of the body 12 in proximal direction 2. By providing a dose indication window 52 at a proximal portion of the body 12, as illustrated in FIG. 6, the size, e.g. the standard units of the actually set dose can be visually indicated.

The extended dosing arrangement 26, 18, 17 may then become subject to a distally directed depression, which is to be conducted and induced by a user by depressing the proximally located dose button 17 in distal direction 1. As further described in detail in WO 2004/078239 A1, WO 2004/078240 A2 or WO 2004/078241 A1 once a dose has been set by screwing the dosing arrangement 26, 17, 18 out of the housing 12, the size of the dose may be corrected at any time by appropriately rotating the dosing arrangement 26, 18, 17 in a respective opposite direction.

When excerting distally directed pressure to the dose button 17 for dispensing of a previously set dose, the dosing arrangement, in particular the dose dial sleeve 26, the dose dial member 18 as well as the dose button 17 become subject to a small but detectable distally directed but non-rotational displacement by way of which a clutch mechanism of the drive mechanism 20 of the drug delivery device 10 appropriately engages in order to operably engage the dose button 17 with the piston rod 25.

The monitoring device 30 is schematically illustrated in different views and configurations in FIGS. 2 to 5. The monitoring device 30 comprises a fastening member 32, which is to be releasably fastened to the body or housing 12 of the drug delivery device 10. In particular, the fastening member 32 may either positively or frictionally engage with the outer circumference of the housing 12. For instance, the fastening member 32 may be clipped or snapped onto the housing 12. The fastening member 32 may therefore comprise a somewhat hollow and arcuate-shaped structure that cooperates with the outer geometry and surface structure of the housing 12 of the drug delivery device.

The fastening member 32 may serve as a kind of housing of the monitoring device 30 and may therefore provide a support for various or even all individual components of the monitoring device 30 as they are mentioned and explained below.

The monitoring device 30 comprises a sliding member 40, extending in longitudinal or axial direction, and being of slab-like or elongated shape. The sliding member 40 comprises an engaging member 42 at its proximal end, which is adapted to abut against a proximal face of the dose button 17 of the dosing arrangement 26, 18, 17 of the drug delivery device 10. All other components of the dosing arrangement, in particular the dose dial sleeve 26 and the dose dial member 18 remain substantially accessible to the user. This way, the dose dial member 18 may be gripped by the user in order to initiate a dose setting procedure, by way of which the dosing arrangement as shown in FIGS. 2 and 4 is transferred from an initial configuration into an extended configuration as illustrated in FIGS. 3 and 5. Due to the axial abutment between the dose button 17 and the engaging member 42, the sliding member 40 is dragged in proximal direction 2 and therefore follows the proximally directed displacement of the dosing arrangement 26, 18, 17.

The monitoring device further comprises a first sensor arrangement 36, 46 and a second sensor arrangement 38, 48. Each sensor arrangement 36, 46, 38, 48 comprises a sensor 36, 38 and a corresponding scale 46, 48, by way of which the screw like rotative and axial displacement of the dosing arrangement 26, 18, 17 can be separately detected and quantitatively determined.

The first sensor arrangement comprises a sensor 36 provided on the shaft of the sliding member 40 of the monitoring device 30 and further has a first scale 46, which is engageable with or which is provided on the outer circumference of the dose dial member 18 of the drug delivery device. Depending on the type of sensor 36, which may be implemented as an optical, haptic, electrical or magnetic sensor, the first scale 46 is either to be manually arranged on the outer circumference of the dose dial member 18 or the first sensor 36 is enabled to e.g. visually detect a rotation of the dose dial member 18, e.g. on the basis of an optic inspection of its circumfering surface. For instance, the first sensor 36 may comprise optical transmitting and detecting means, e.g. adapted to evaluate a reflected speckle pattern provided by a comparatively rough surface of the dose dial member 18.

Additionally, or alternatively, the first scale may comprise an incremental encoding, which is either integrally formed or embedded on or in the dose dial member 18 or which is to be separately arranged at its outer circumference. Due to the axial abutment of the dosing arrangement 26, 18, 17 and the engaging member 42 of the sliding member 40, a relative axial position between the first sensor 36 and the first scale 46 is substantially fixed and remains constant irrespective of the configuration of the drug delivery device 10. The first sensor arrangement 36, 46 is therefore preferably adapted to incrementally detect any rotational movement of the dose dial member 18 relative to the sliding member 40 and/or relative to the housing 12.

The monitoring device 30 further comprises a second sensor arrangement 38, 48 comprising a second sensor 38 arranged on or in the fastening member 32 and having a second scale 48 provided on and extending along the slab-like sliding member 40 of the monitoring device 30. By way of the second sensor arrangement 38, 48 an axial relative displacement between the sliding member 40 relative to the fastening member 32 can be quantitatively detected. Accordingly, also the second scale 48 preferably comprises an incrementally encoded scale 48 allowing to precisely determine the axial path length the sliding member 40 moves during a proximally directed dose setting and/or during a distally directed dose dispensing procedure.

In normal operation, hence, during dose setting, both sensors 36, 38 simultaneously generate and provide respective first and second signals to a processing member 34 of the monitoring device 30. As soon as first and second signals are obtained in synchronism, the dosing arrangement 26, 18, 17 is moved in a screw-like way.

It is only at the beginning and at the end of a dose dispensing procedure that the dosing arrangement 26, 18, 17 is subject to a small by measurable axial and non-rotational displacement relative to the housing 12. By continuously comparing the signals obtainable form the first and the second sensors 36, 38 the processing member 34 adapted to process said signals may precisely distinguish and recognize the beginning and the end of a dose dispensing procedure.

This way, even a dose correcting displacement of the dosing arrangement can be precisely detected, such that the monitoring device may precisely detect, monitor and store such dispensing parameters, which reflect the amount of the medicament, which has been actually dispensed by the drug delivery device 10.

When for instance a dose correcting movement of the dosing arrangement 26, 18, 17 has to be conducted, the dose dial member 18 is simply to be rotated in an opposite direction compared to an initial dose setting screwing motion. Moreover, the monitoring device 30 is also applicable to detect that a dose previously set has only dispensed incompletely. When, for instance, distally directed displacement of the dosing arrangement 26, 18, 17 stops prior to arrive at an initial configuration as for instance shown in FIGS. 3, 4, the clutch of the drive mechanism 20, which is not particularly illustrated here, may disengage, thereby causing a purely axially directed but non-rotational movement of the dosing arrangement 26, 18, 17.

As soon as such a repeated clutch movement has been detected by the continuous processing and comparison of the signals provided by the first and the second sensor arrangements 36, 38, 46, 48, the processing member 34 will stop to record the respective dose dispensing procedure.

In the enlarged view according to FIG. 6 a scale member 50 comprising or providing the first scale 46 therein is illustrated, comprising a ring structure and which is adapted to frictionally engage with the dose dial member 18. Moreover, a dose indication window is shown through which a dose size indicating scale provided on the outer circumference of the dose dial sleeve 26 is presented. The housing 12 of the drug delivery device 10 further comprises at least one raised portion 54 extending radially outwardly from the substantially tubular shaped housing 12.

The raised portion 54 may serve as a symmetry-breaking feature in order to attach the releasable monitoring device 30 in a single predefined orientation on the housing 12. In a similar way, also the dose dial member 18 among numerous raised portions 58 may feature a particular raised or recessed portion 56 to mount the first scale member 50 only in a predefined orientation onto the dose dial member 18. By mechanically encoding the dose dial member 18, the first scale member 50 to be mounted thereon and by further mechanically encoding the fastening member 32 and the housing 12 of the drug delivery device 10, the monitoring device 30 and the first scale member 50 are to be assembled in a particular or predefined way, in which the mutually interacting components, in particular first and second sensors 36, 38 and first and second scale members 46, 50, 48 may be readily calibrated.

LIST OF REFERENCE NUMERALS

1 distal direction
2 proximal direction
10 drug delivery device
12 housing
13 inspection window
14 protective cap
16 cartridge holder
17 dose button
18 dose dial member
20 drive mechanism
22 cartridge
25 piston rod
26 dose dial sleeve
30 monitoring device
32 fastening member
34 processing member
36 sensor
38 sensor
40 sliding member
42 engaging member
46 scale
48 scale
50 scale member
52 dose indication window
54 raised portion
56 raised portion
58 raised portion

The invention claimed is:

1. A monitoring device for monitoring operation of a drug delivery device, the monitoring device comprising:
    a fastening member configured to releasably attach the monitoring device to an axially elongated housing of the drug delivery device;
    a sliding member shiftable relative to the fastening member in an axial direction and being adapted to operably engage with a dose setting component of the drug delivery device to follow an axial displacement of the dose setting component relative to the housing;
    a first sensor arrangement configured to detect a rotation of the dose setting component relative to the fastening member;
    a second sensor arrangement configured to detect an axial displacement of the sliding member relative to the fastening member; and
    a processing member coupled to the first and to the second sensor arrangements and configured to process first and second signals obtainable from the first and from the second sensor arrangements for determining of a size of a dose dispensed or set by the drug delivery device,
    wherein at least one of the first and the second sensor arrangements comprises a scale and a sensor cooperating with the scale, wherein the sensor and the scale are subject to a relative displacement
    when the dose setting component is subject to a movement relative to the housing, or
    when the sliding member is subject to an axial displacement relative to the fastening member.

2. The monitoring device according to claim 1, wherein the first sensor arrangement is adapted to quantitatively determine a rotational displacement of the dose setting component relative to the housing and wherein the second sensor arrangement is adapted to quantitatively determine an axial displacement of the dose setting component relative to the housing.

3. The monitoring device according to claim 1, wherein the first sensor arrangement comprises a first scale attachable to the rotatable dose dial member of the drug delivery device and comprises a first sensor arranged on the sliding member and cooperating with the first scale.

4. The monitoring device according to claim 1, wherein the second sensor arrangement comprises a second scale attachable to the sliding member and comprises a second sensor arranged on the fastening member and cooperating with the second scale.

5. The monitoring device according to claim 1, wherein the sliding member comprises an engaging member at a proximal end to axially abut with a dose button at the proximal end of the drug delivery device.

6. The monitoring device according to claim 1, wherein at least one of the first and the second scale is incrementally encoded in a direction of movement relative to one or both of the first or second sensor.

7. The monitoring device according to claim 1, wherein the processing member is adapted to distinguish between a dose setting and a dose dispensing procedure of the drug delivery device on the basis of a comparison of first and second signals obtainable from the first and the second sensor arrangements, respectively.

8. The monitoring device according to claim 1, wherein an asynchronicity between the first signal and the second signal is indicative of one of both of a beginning or an end of a dose dispensing procedure of the drug delivery device.

9. The monitoring device according to claim 1, wherein a temporal offset between first and second signals is indicative of one or both of a beginning or an end of a dose dispensing procedure.

10. The monitoring device according to claim 1, wherein the processing member is adapted to one or both of record or store one or more of the size, the time, or other properties of a dose dispensed by the drug delivery device only when receiving the first signal in synchronous with the second signal.

11. The monitoring device according to claim 1, wherein the sensor is based on one of a tactical, optical, magnetic or electrical sensor principle.

12. The monitoring device according to claim 11, wherein the scale is tactilely, optically, magnetically or electrically encoded and wherein the scale is encoded in correspondence with the sensor principle of the sensor.

13. A drug delivery device for setting and dispensing a dose of medicament, comprising:
- a housing of substantially tubular shape to accommodate a drive mechanism having a piston rod to operably engage with a piston of a cartridge containing a medicament;
- at least one dosing arrangement axially displaceable in a proximal direction for setting of a dose and being subsequently displaceable in an opposite, distal direction to conduct a dose dispensing procedure; and
- a monitoring device according to claim 1 being releasably attached to the housing by the fastening member and having the sliding member operably engaged with the at least one dose setting component.

14. The drug delivery device according to claim 11, wherein the dosing arrangement comprises a rotatable dose dial member and a dose button depressible in distal direction which become subject to a combined rotating and axial motion during dose setting and during dose dispensing.

15. The drug delivery device according to claim 11, further comprising a cartridge holder arranged at a distal end at the housing and having a cartridge arranged therein which is at least partially filled with a medicament.

* * * * *